(12) United States Patent
Vose et al.

(10) Patent No.: US 10,714,226 B2
(45) Date of Patent: Jul. 14, 2020

(54) STRONTIUM SEALED SOURCE

(71) Applicant: ILLINOIS TOOL WORKS INC., Glenview, IL (US)

(72) Inventors: Mark W. Vose, Windham, NH (US); Mark G. Shilton, Chelmsford, MA (US); Jason W. Bourn, Stratham, NH (US)

(73) Assignee: QSA GLOBAL, INC, Burlington, MA (US)

( * ) Notice: Subject to any disclaimer, the term of this patent is extended or adjusted under 35 U.S.C. 154(b) by 233 days.

(21) Appl. No.: 15/571,310

(22) PCT Filed: Mar. 15, 2016

(86) PCT No.: PCT/US2016/022437
§ 371 (c)(1),
(2) Date: Nov. 2, 2017

(87) PCT Pub. No.: WO2016/178746
PCT Pub. Date: Nov. 10, 2016

(65) Prior Publication Data
US 2018/0358142 A1    Dec. 13, 2018

Related U.S. Application Data

(60) Provisional application No. 62/158,091, filed on May 7, 2015.

(51) Int. Cl.
*G21G 4/06*    (2006.01)
*A61N 5/10*    (2006.01)
*A61F 9/007*    (2006.01)

(52) U.S. Cl.
CPC ............. *G21G 4/06* (2013.01); *A61N 5/1001* (2013.01); *A61F 9/007* (2013.01); *A61M 2210/0612* (2013.01)

(58) Field of Classification Search
CPC ........ A61N 5/1001–1029; A61F 9/007; A61M 2210/0612; G21G 4/06–08
See application file for complete search history.

(56) References Cited

U.S. PATENT DOCUMENTS

| | | | |
|---|---|---|---|
| 4,284,887 A | 8/1981 | Kusumoto et al. |
| 6,907,106 B1 | 6/2005 | McIntyre et al. |
| 7,070,554 B2 | 7/2006 | White et al. |
| 8,430,804 B2 | 4/2013 | Brigatti et al. |
| 9,873,001 B2 | 1/2018 | Lutz et al. |
| 2010/0004499 A1 | 1/2010 | Brigatti et al. |

(Continued)

FOREIGN PATENT DOCUMENTS

| | | |
|---|---|---|
| CN | 101951965 | 1/2001 |
| CN | 1413748 | 4/2013 |

(Continued)

OTHER PUBLICATIONS

International Search Report issued in PCT/US2016/022437 dated Aug. 17, 2016.

*Primary Examiner* — Thaddeus B Cox
(74) *Attorney, Agent, or Firm* — McCarter & English, LLP (57) ABSTRACT

The disclosure pertains to a strontium-90 sealed radiological or radioactive source, such as may be used with treatment of the eye or other medical or industrial processes. The sealed radiological source includes a toroidal shaped strontium radiological insert within an encapsulation. The encapsulation includes increased shielding in the center thereof.

8 Claims, 7 Drawing Sheets

(56) References Cited

U.S. PATENT DOCUMENTS

| | | |
|---|---|---|
| 2013/0240761 A1 | 9/2013 | Wang |
| 2016/0375267 A1 | 12/2016 | Lutz et al. |

FOREIGN PATENT DOCUMENTS

| | | |
|---|---|---|
| EP | 1529554 | 5/2005 |
| GB | 2350718 | 12/2000 |
| JP | 2011-508654 | 3/2011 |
| WO | 2000/075692 | 12/2000 |
| WO | 2015/105539 | 7/2015 |

STRONTIUM SEALED SOURCE

This application is a National Phase Application of PCT International Application No.: PCT/US2016/022437, filed on Mar. 15, 2016, which claims priority under 35 U.S.C. 119(e) of U.S. provisional application Ser. No. 62/158,091, filed on May 7, 2015, the contents of which is hereby incorporated by reference in its entirety and for all purposes.

BACKGROUND OF THE DISCLOSURE

Field of the Disclosure

The disclosure pertains to a strontium-90 sealed source, such as may be used with treatment of the eye or other medical, brachytherapeutic or industrial processes. In particular, a relatively constant absorbed dose rate is sought throughout a target volume of tissue of therapeutic interest that is to be treated with radiation (hereinafter referred to as "a flat radiation profile").

Description of the Prior Art

The prior art of radiological or radioactive sources of various types for medical, industrial and other processes is well-developed. For example, U.S. Pat. No. 8,430,804, entitled "Methods and Devices for Minimally-Invasive Extraocular Delivery of Radiation to the Posterior Portion of the Eye", issued on Apr. 30, 2013 to Brigatti et al., and assigned on its face to Salutaris Medical Devices, Inc., discloses an applicator for minimally-invasive delivery of beta radiation from a radionuclide brachytherapy source to the posterior portion of the eye. In particular, this is adapted for the treatment of various diseases of the eye, such as, but not limited to, wet age-related macular degeneration. Other prior art includes U.S. Pat. No. 7,070,554 entitled "Brachytherapy Devices and Methods of Using Them", issued on Jul. 4, 2006 to White et al., and assigned on its face to Theragenics Corporation and U.S. Pat. No. 6,443,881, entitled "Ophthalmic Brachytherapy Device", issued on Sep. 3, 2002 to Finger.

While this prior art is well-developed and suited for its intended purposes, further improvements are sought in the radioactive sources used in the disclosed devices. In particular, a collimated distribution of radiation, rather than an isotropic (spherical "4π") distribution of radiation, would allow a radiological source to direct radiation at the tissues under treatment, while reducing radiation directed at surrounding tissues which are not under treatment.

OBJECTS AND SUMMARY OF THE DISCLOSURE

It is therefore an object of the present disclosure to provide improvements in the radiological sources used in brachytherapy and in other medical or industrial applications. In particular, it is an object of the present disclosure to provide improved radiological sources for known applicators for treatment of diseases of the eye, including, but not limited to, wet age-related macular degeneration. These radiological sources are intended to concentrate the radiation on the diseased tissue, rather than using isotropic radiation which would expose more of the surrounding healthy tissue to unnecessary radiation.

This and other objects are attained by providing a beta radiological source, typically containing strontium-90, wherein the radiological insert has increased radioactivity around its periphery and less radioactivity at its center. This may be achieved by a toroidal or annular shape, (such as a donut-type shape with a hole or aperture in the middle) or with the central portion of a disk having reduced thickness or reduced radioactivity content. This is further achieved by providing an encapsulation with increased shielding in the center of the face from which the therapeutic radiation is emitted, thereby substantially attenuating the radiation emitted from the central portion of a source. A further alternative uses a beta radiation collimator grid.

BRIEF DESCRIPTION OF THE DRAWINGS

Further objects and advantages of the disclosure will become apparent from the following description and from the accompanying drawings, wherein.

DETAILED DESCRIPTION OF THE PREFERRED EMBODIMENTS

Figure 1A:
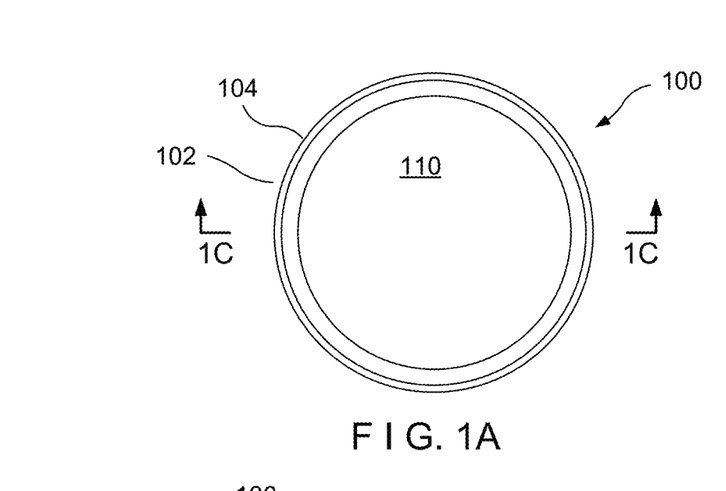
FIG. 1A is a top view of an embodiment of the radiological source of the present disclosure.
Figure 1B:
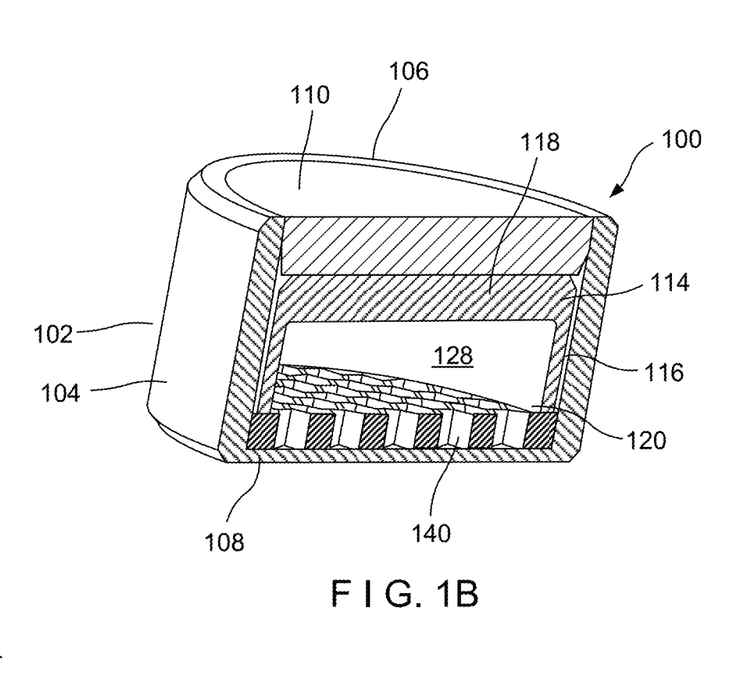
FIG. 1B is a perspective, cut-away view of an embodiment of the radiological source of the present disclosure.
Figure 1C:
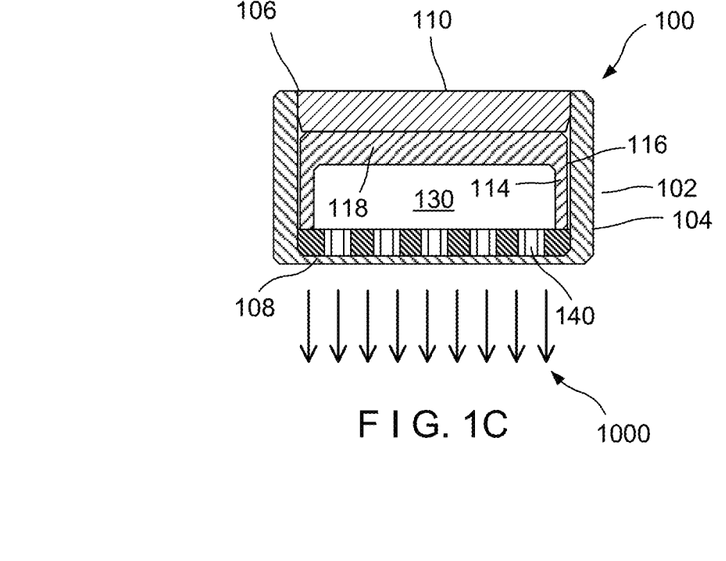
FIG. 1C is a cross-sectional view along plane 1C-1C of FIG. 1A.
Figure 6:
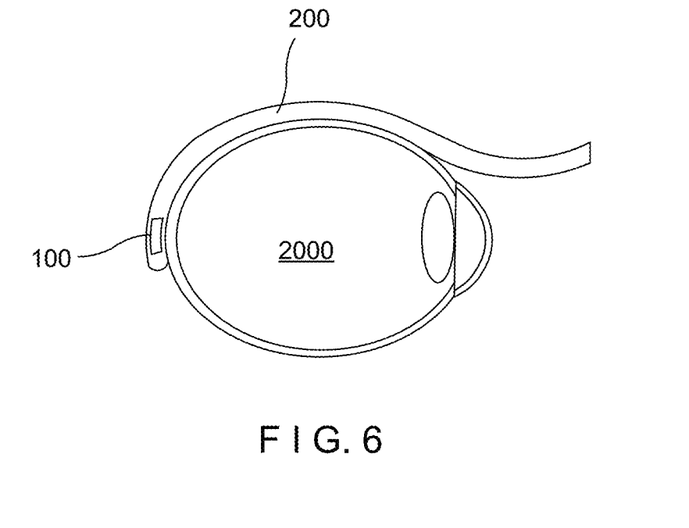
FIG. 6 illustrates a placement of the radiological source with respect to a human eyeball during medical treatment.
Figure 7:
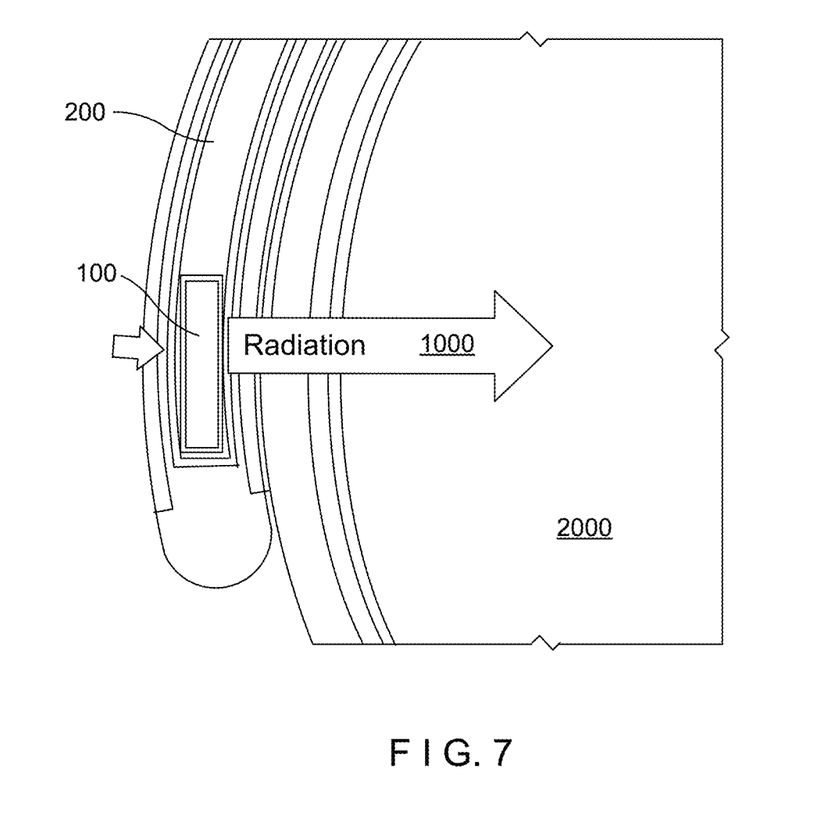
FIG. 7 illustrates a portion of FIG. 6 in greater detail.

Referring now to the drawings in detail wherein like numerals refer to like elements throughout the several views, one sees that FIGS. 1A, 1B and 1C illustrate an embodiment of the radiological (or radioactive) source 100 of the present disclosure. Radiological source 100 includes an outer source encapsulation 102, typically made from a titanium alloy, stainless steel or similar material with suitable beta absorption and transmission characteristics. Outer source encapsulation 102 includes outer cylindrical walls 104, an open circular top 106 and a circular floor 108 forming a closed bottom. A circular cap 110, similarly typically made from a titanium alloy, stainless steel or similar material, is placed over the open circular top 106 and welded in place after all assembly has been completed, thereby resulting in a low cylindrical configuration. A cylindrical inner source encapsulation-nest 114, similarly typically made from a titanium alloy, stainless steel or similar material includes inner cylindrical walls 116, a closed circular top 118 and an open circular bottom 120. The interior of inner cylindrical walls 116 creates a generally cylindrical volume or cavity 128 (see FIG. 1B, showing the cavity without a strontium-90 insert) which holds strontium-90 insert 130 (beta radiation source, see FIG. 1C), which is typically in an insoluble refractory material such as a ceramic or glass or a refractory-metal composite form such as a Strontium-90 compound mixed with a low density metal such as beryllium or aluminum. A beta emission collimator grid 140, typically of a honeycomb configuration, is positioned immediately above, and contacting, the circular floor 108 or closed bottom of outer source encapsulation 102 and immediately below, and contacting, the strontium-90 insert 130 and the lower edge of inner cylindrical walls 116 of inner source encapsulation 114. The resulting radiological source 100 has a distribution of beta radiation 1000 (see FIG. 1C) which is not isotropic but which is substantially collimated (in part, by the function of collimator grid 140) so as to direct a greater portion of the beta radiation 1000 straight downwardly, in the illustrated orientation of FIG. 1C. The resulting radiological source 100 is intended to be particularly well-adapted for use with the medical instrument of U.S. Pat. No. 8,430,804, with the distribution of radiation intended to allow the medical professional to direct the radiation to the treatment volume of the patient while minimizing the amount of unnecessary radiation directed to the surrounding healthy tissues. See, for example, FIGS. 6 and 7 which illustrate a medical instrument 200 positioning the radiological source 100 behind a human eyeball 2000 and directing radiation horizontally into the human eyeball 2000.

It is noted that the strontium-90 beta radiation insert 130 may be made of various materials, such as a strontium ceramic, strontium glass, or a collection of tightly packed ceramic beads (of various possible shapes) or a refractory-metal composite. Refractory ceramics and glasses containing Strontium-90 can be made from a wide variety of materials in combination, such as those containing metal oxides of aluminum, silicon, zirconium, titanium, magnesium, calcium amongst others. It is envisioned that other additional materials may be selected from, but not limited to, such strontium-90 compounds as $SrF_2$, $Sr_2P_2O_7$, $SrTiO_3$, $SrO$, $Sr_2TiO_4$, $SrZrO_3$, $SrCO_3$, $Sr(NbO_3)^2$, $SrSiO_3$, $3SrO.Al_2O_3$, $SrSO_4$, $SrB_6$, $SrS$, $SrBr_2$, $SrC_2$, $SrCl_2$, $SrI_2$ and $SrWO_4$. Additional, beta emitters based on materials other than strontium-90 may also be compatible with this disclosure.

Figure 2A:
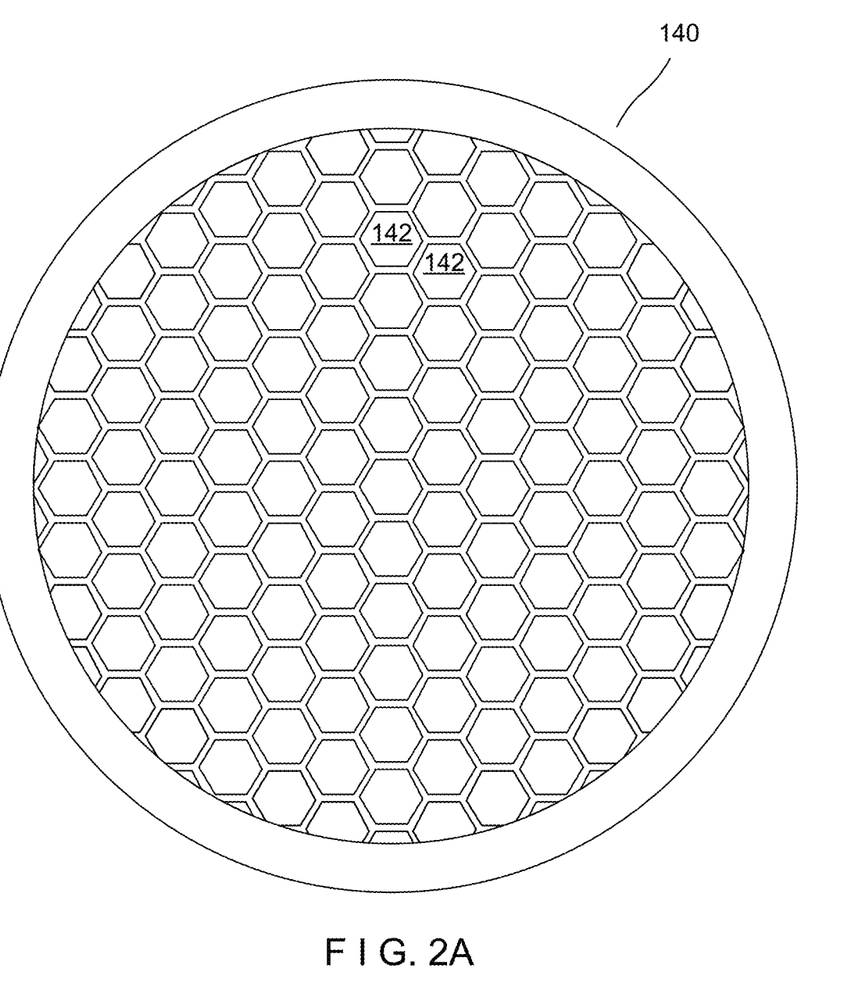
FIG. 2A is a plan view of the beta radiation collimator grid of the present disclosure.
Figure 2B:
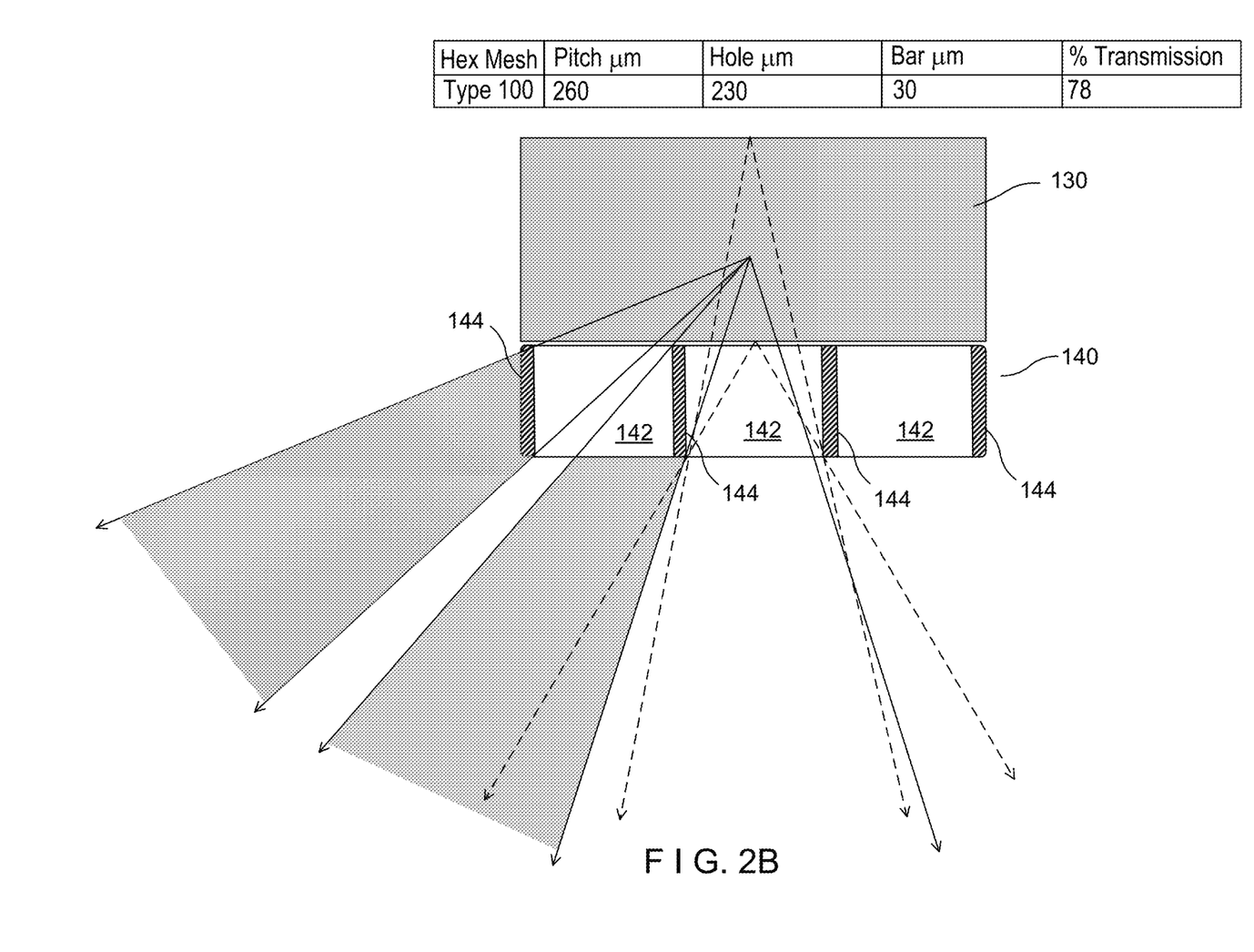
FIG. 2B illustrates the operation of the beta radiation collimator grid collimator grid in greater detail.

FIGS. 2A and 2B disclose the beta collimator grid 140 in further detail. The object of the beta collimator grid 140 is to block or absorb a significant portion of the non-orthogonal beta emissions while blocking or absorbing very little of the direct or orthogonal beta emissions from the strontium-90. The beta collimator grid 140 has a plurality of honeycomb-shaped open cells 142 (not drawn to scale) separated by walls 144 (see FIG. 2B for walls 144). The non-orthogonal beta emissions strike the walls 144 of the honeycomb-shaped cells 142 and are substantially absorbed, while the direct or orthogonal beta emissions pass through the openings or passageways of open cells 142 without striking the walls 144. In a typical example illustrated in FIGS. 2A and 2B, the total thickness is 250 microns, the bar thickness is 30 microns, with a cell pitch of 260 microns and an aperture diameter of 230 microns, resulting in an expected direct ray transmission of 78%. That is, 22% of the direct ray beta emission is attenuated. Those skilled in the art, after review of this disclosure, will recognize that different dimensions and numerical values may be used for similar applications. It is envisioned that some embodiments may include the honeycomb-shaped cells 142 around the outer circumference of the collimator grid 140, with essentially 100 percent transmission near the center of the collimator grid 140. This would increase the direct ray emission and non-orthogonal emissions would likely impart their energy in a therapeutic region which the direct rays are also targeting. The other advantage of using a collimator grid in combination with a disk-shaped source is a flat dose profile (i.e. a profile achieving a constant absorbed dose rate throughout a target volume of tissue of therapeutic interest that is to be treated with radiation). The effect of this is that tissue at a certain depth and with a certain volume will receive the same dose rate and uniform therapeutic dose without under or over-exposure of different parts of the therapeutic volume of interest. While a honeycombed hexagonal configuration is illustrated, the collimator grid 140 could be square mesh or any other tightly nesting mesh geometry. The collimator grid 140 can be selected from various metals or non-metals which would absorb beta emissions, but which would survive normal operating conditions and potential accident hazard conditions such as an 800° C. fire, while not adversely interacting with other source components. Typical preferred materials include iron alloys, nickel alloys, molybdenum alloys, copper alloys, gold alloys, carbon and silicon. Those skilled in the art, after review of the present disclosure, will recognize that additional materials may be used for various applications. Additionally, the collimator grid 140 may be etched into the circular floor 109 of radiological source 100.

Collimation is more effective with photons than with beta particles because photons scatter less in surrounding absorbers than beta particles do. Photons are less easily attenuated (scattering less), beta particles are highly attenuated (scattering more, as beta particles have the same mass and charge as electrons so their collisions impart more energy per collision). Beta particles are also typically emitted with a spectrum of energies from zero to the maximum (2.28 meV in the case of Y-90, a decay product of Strontium-90), so their attenuation and scatter characteristics differ greatly to mono-energetic photons, which are attenuated only by electromagnetic field interactions.

In order to produce a flat dose profile at the correct tissue depth in front of the presently disclosed beta source, the source output typically needs to accentuate the difference in dose rate at the center versus dose rate in the periphery at the source surface. In other words, if the dose profile were to be flat at the source surface, it would not then also be flat at a distance away from the source surface due to effects of beta scattering in tissue. Therefore, it is typically desired to produce an annular dose profile at the source surface which is much lower in the center than in the periphery, so that it will become flat at the desired depth in tissue due to beta scattering in the tissue. At further distances from the source, the tissue dose profile would become progressively more spherical as more scatter and attenuation occurs.

The absorbing tissue effectively acts as a source of scattered lower-energy radiation, which makes the dose profile less collimated and more spherical at distances further removed from the source.

Figure 3:
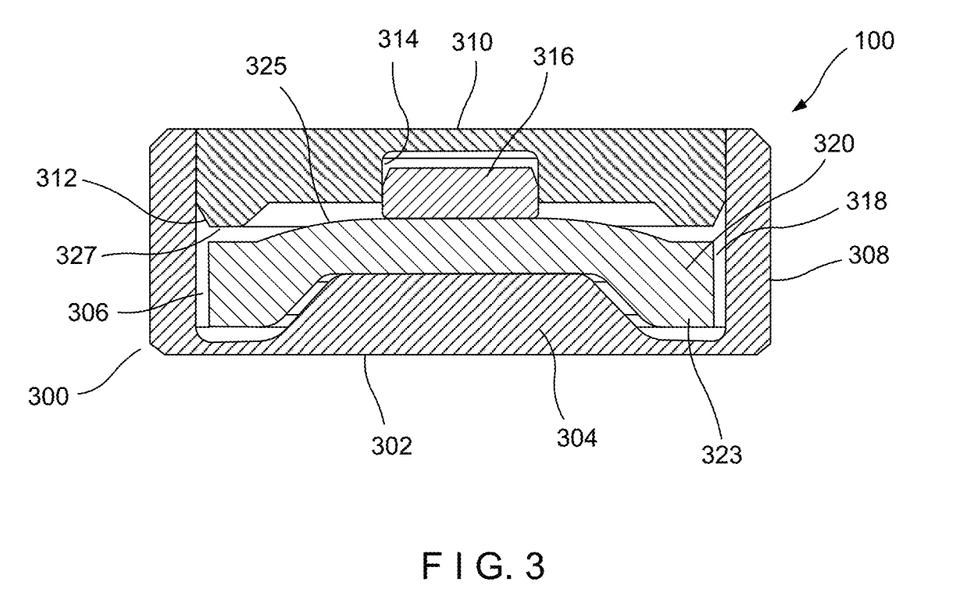
FIG. 3 is a cross-sectional view of a further embodiment of a radiological source of the present disclosure.
Figure 4:
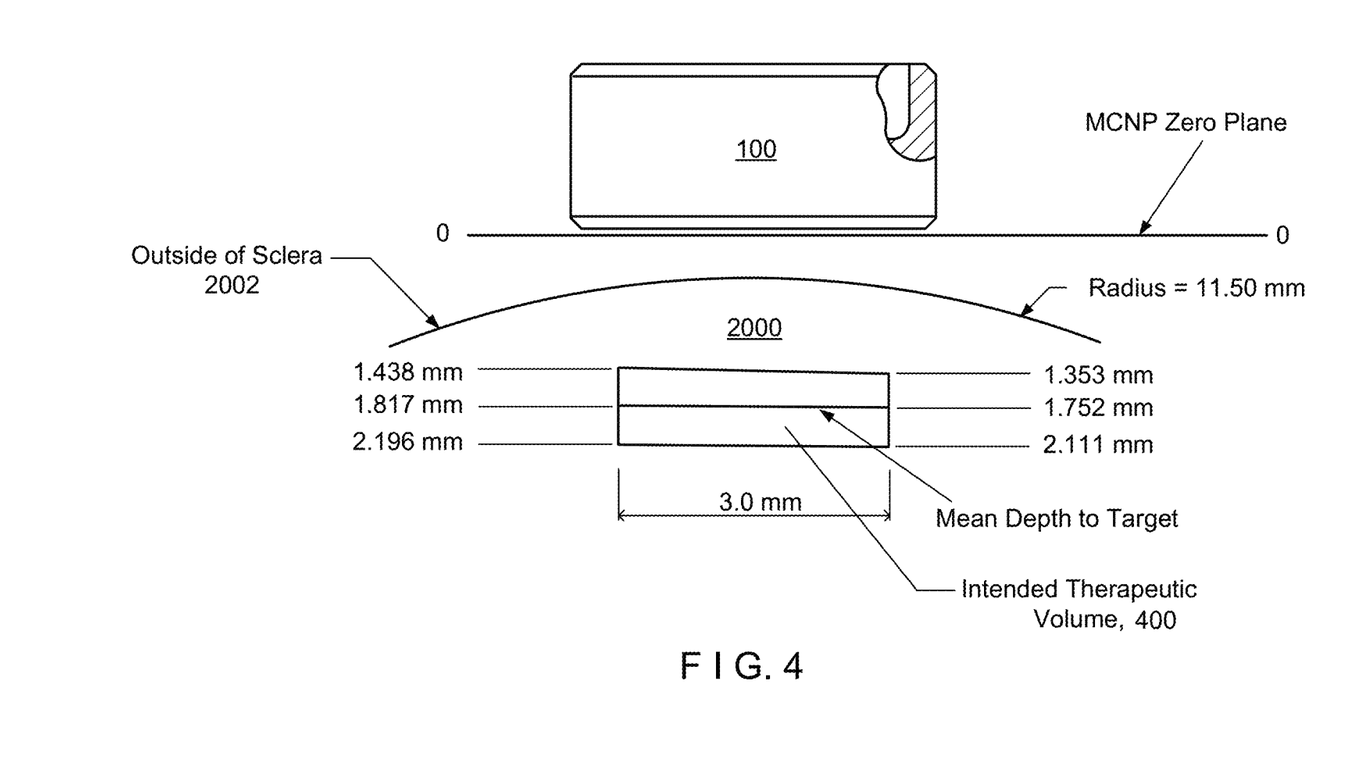
FIG. 4 is an illustration relating to the radiation dose profile generated by the radiological source of FIG. 3.

FIG. 3 illustrates a cross-sectional view of a further embodiment of the radiological source 100. The radiological source 100 is substantially rotationally symmetric, including cylindrical, annular and toroidal shapes. A capsule body 300, typically made of titanium or stainless steel, includes a lower floor 302 with a central plateau 304 thereby forming a toroidal channel 306 between the central plateau 304 (thereby increasing the beta shielding in central portions of the lower floor 302) and the outer cylindrical wall 308 of the capsule body 300. The upper edge of outer cylindrical wall 308 forms a circular opening for receiving outer lid 310 which is generally cylindrical but includes a chambered lower circular edge 312 and further includes a central cylindrical blind opening 314 for receiving telescoping inner lid 316, and typically forming a tight friction fit therebetween. Outer lid 310, which is typically made of titanium or stainless steel and illustrated with an interior circumferential toroidal ridge 327, is typically welded to capsule body 300, using conventional standards of the industry. Strontium-90 radiological insert 318 (similar to insert 130 in previous embodiments) includes an upper circular or disk-shaped portion 320 which is engaged between a lower edge of telescoping inner lid 316 and central plateau 304 of capsule body 300. This configuration is intended to reduce rattling of the strontium-90 radiological insert 318. The upper surface of strontium-90 radiological insert 318 includes a convex central region 325. This convex central region 325 is intended to reinforce the structure and avoid or minimize warping and possible delamination during production. Strontium-90 radiological insert 318 further includes a downwardly extending circumferential toroidal portion 323 which extends into toroidal channel 306 of capsule body 300.

The toroidal shape of the strontium-90 radiological insert 318, with its thickened periphery, leads to increased radiation emission around the periphery and a reduced radiation output within the center. This, in combination with the increased beta shielding in the central area of central plateau 304, results in a flat beam profile, achieving a more constant absorbed dose rate throughout a target volume of tissue of therapeutic interest that is located in front of the source) as illustrated in FIG. 5, wherein typical values are given for a radiological source 100 of a diameter of 4.05 millimeters and a maximum height of 1.75 millimeters. In the given example, a intended therapeutic volume 400 with a diameter of 3.0 millimeters and a depth of 1.438 to 2.196 millimeters (with a mean depth to target of 1.817 millimeters from the lower surface of the radiological source 100) in a first case or a depth of 1.353 to 2.111 millimeters (with a mean depth to target of 1.752 millimeters from the lower surface of the radiological source 100) in a second case. A radius of 11.50 millimeters is typical for the sclera 2002 (outer covering) of a human eyeball 2000 (see also FIGS. 6 and 7). Those skilled in the art, after review of this disclosure, will understand that different structural parameters will result in different radiation distributions, as may be required by the specific application.

Figure 5A:
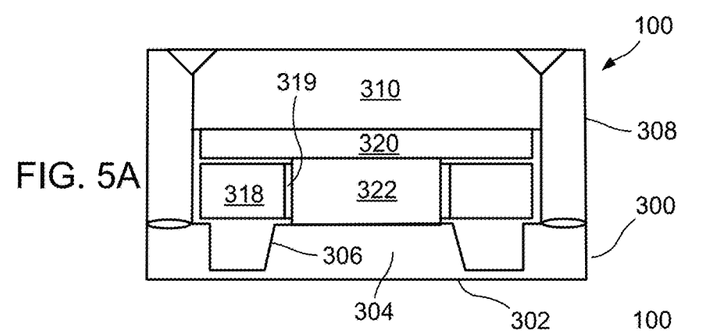
FIGS. 5A-5F illustrates various further embodiments of the radiological source of the present disclosure.

FIGS. 5A through 5F illustrate six further design embodiments of radiological source 100 of the present disclosure. The radiological source 100 of FIG. 5A is very similar to FIG. 3 and includes capsule body 300 includes a lower floor 302, the interior wall of the lower floor 302 including a central plateau 304 on the interior thereof thereby forming a toroidal channel 306 between the central plateau 304 and the outer cylindrical wall 308 of the capsule body 300. The upper edge of outer cylindrical wall 308 forms a circular opening for receiving outer lid 310 which is generally cylindrical. Outer lid 310 is typically welded to capsule body 300, using conventional standards of the industry. Strontium-90 radiological insert 318 is toroidally shaped by rotating a rectangular cross-section about the central axis thereby resulting in a central passageway 319. Toroidally-shaped radiological insert 318 is positioned above the toroidal channel 306, and supported by central plateau 304 and shoulder 308A, 308B formed within an interior of outer cylindrical wall 308. A cylindrical disk-shaped spacer 320, typically made of titanium or stainless steel, is positioned between the radiological insert 318 and the lower surface of the outer lid 310. Additionally, a cylindrical shielding insert 322, typically made from titanium or stainless steel, inserted within the central aperture 319. The shape of the strontium-90 radiological insert 318 leads to increased radiation output around the periphery, with a reduced radiation output within the central aperture 319. This, in combination with the increased shielding in the central area of central plateau 304 and the cylindrical shielding insert 322, results in a flat beam profile, achieving a more constant absorbed dose rate throughout a target volume of tissue of therapeutic interest that is located in front of the source (i.e., anisotropic) characteristic of the resulting beta radiation.

Figure 5B:
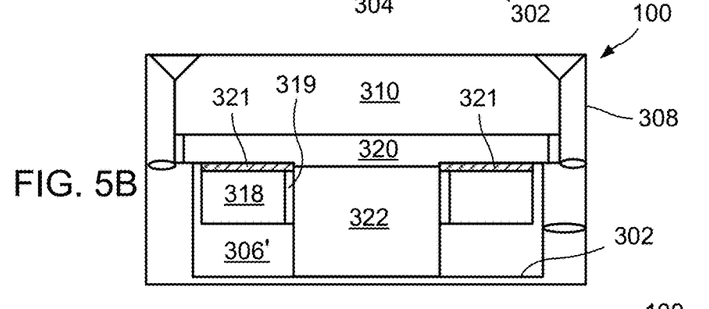

The embodiment of radiological source 100 in FIG. 5B is similar to that of FIG. 5A. The interior wall of lower floor 302 is generally planar without the central plateau of FIG. 5A. The toroidal-shaped strontium-90 radiological insert 318 is secured to cylindrical disk-shaped spacer 320 by a low-melting glass bond 321 or similar configuration. Cylindrical shielding insert 322 extends from spacer 320 to the inner wall of lower floor 302, thereby resulting in a configuration with a toroidal-shaped void 306' below the toroidal-shaped strontium-90 radiological insert 318. The shape of the strontium-90 radiological insert 318 leads to an increased radiation source around the periphery, with a removal of a source of radiation within the central aperture 319. This, in combination with the increased shielding of the cylindrical shielding insert 322, results in a flat beam profile, achieving a more constant absorbed dose rate throughout a target volume of tissue of therapeutic interest that is located in front of the source).

Figure 5C:
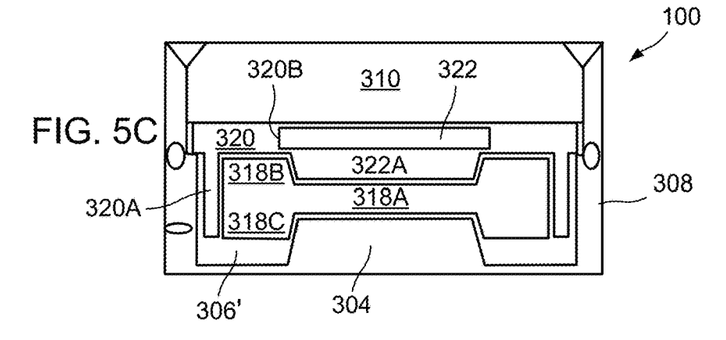

The embodiment of radiological source 100 in FIG. 5C is similar to that of FIG. 5A. The toroidal-shaped strontium-90 radiological insert 318 includes a central cylindrical disk portion 318A and further includes upper and lower toroidal portions 318B, 318C, respectively, extending around the circumference thereof. Additionally, spacer 320 further includes a downwardly extending cylindrical skirt 320A which outwardly abuts the circumference of toroidal-shaped strontium-90 radiological insert 318. Spacer 320 further includes a central cylindrical aperture 320B which receives a variation of shielding insert 322, further including a downwardly extending frusto-conical portion 322A for engaging against central cylindrical disk portion 318A of strontium-90 radiological insert 318 and being positioned within the upper toroidal portion 318B of strontium-90 radiological insert 318. This configuration engages the central cylindrical disk portion 318A between the downwardly extending frusto-conical portion 322A of shielding insert 322 and central plateau 304. Similar to the embodiment of FIG. 5B, a toroidal-shaped void 306' is formed between the lower toroidal portion 318C of strontium-90 radiological insert 318 and the inner wall of floor 302. The shape of the strontium-90 radiological insert 318 leads to an increased radiation source around the periphery, with a reduction in the radiation from cylindrical disk portion 318A. This, in combination with the increased shielding of the central plateau 304, results in a flat beam profile, achieving a more constant absorbed dose rate throughout a target volume of tissue of therapeutic interest that is located in front of the source).

Figure 5D:
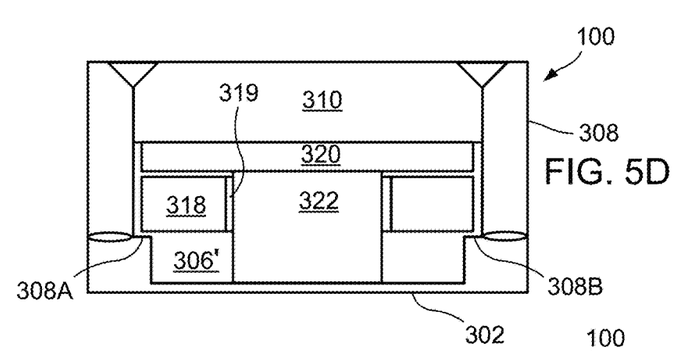

The embodiment of FIG. 5D is similar to that of FIG. 5B. However, the interior of cylindrical wall 308 includes shoulders 308A, 308B for supporting the toroidal-shaped strontium-90 radiological insert 318 above the toroidal channel 306. This may eliminate the need for the low melting glass bond 321 or similar configuration to affix the toroidal-shaped strontium-90 radiological insert 318 to the spacer 320. The shape of the strontium-90 radiological insert 318 leads to an increased radiation source around the periphery, with a removal of a source of radiation within the central aperture 319. This, in combination with the increased shielding of the cylindrical shielding insert 322, results in a flat beam profile, achieving a more constant absorbed dose rate throughout a target volume of tissue of therapeutic interest that is located in front of the source).

Figure 5E:
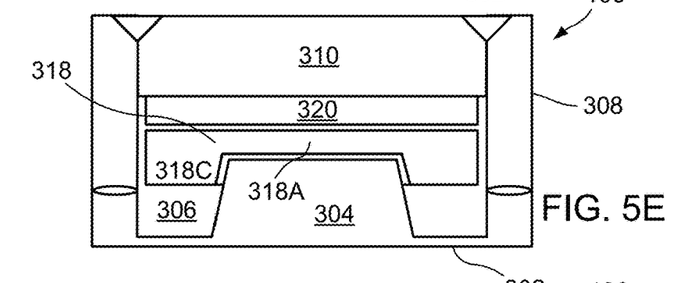

The embodiment of FIG. 5E is similar to that of FIG. 5C. The toroidal-shaped strontium-90 radiological insert 318 includes a central cylindrical disk portion 318A and further includes a lower toroidal portion 318C extending around the circumference thereof. The lack of an upper toroidal portion allows the spacer 320 to be simplified to a cylindrical disk shape. The shape of the strontium-90 radiological insert 318 leads to an increased radiation source around the periphery, with a reduction in the radiation from cylindrical disk portion 318A. This, in combination with the increased shielding of the central plateau 304, results in a flat beam profile, achieving a more constant absorbed dose rate throughout a target volume of tissue of therapeutic interest that is located in front of the source).

Figure 5F:
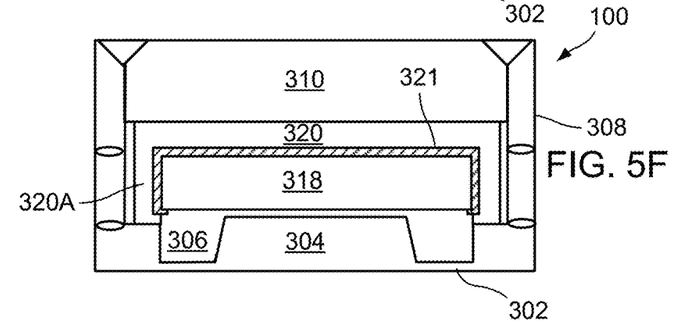

The embodiment of FIG. 5F is similar to that of FIG. 5E. The strontium-90 radiological insert 318 is simplified to a disk shape, rather than a toroidal shape. Additionally, spacer 320 further includes a downwardly extending cylindrical skirt 320A which outwardly abuts the circumference of toroidal-shaped strontium-90 radiological insert 318. The strontium-90 radiological insert 318 is secured to cylindrical disk-shaped spacer 320 by a low-melting glass bond 321 so as to be suspended above central plateau 304 and toroidal channel 306. It is envisioned that this embodiment could further have the strontium-90 radiological insert 318 contacting and being supported, at least in part, by central plateau 304.

Further alternatives to the present disclosure include fixation of the active insert using glass, such as glass pre-melted into a stainless steel insert, glass powder co-compacted with a ceramic and glass powder mixed with a ceramic and then compacted. Additionally, alternatives include fixation of the active insert using mechanical methods such as soft materials such as copper, silver, aluminum, etc. or the use of springs of various types (wave, conical, folded disk, etc.). Further alternatives include active insert centering features to prevent positional errors such as tapered ceramic disks or a disk with an aperture or protrusion which interfaces with the capsule lid.

Thus the several aforementioned objects and advantages are most effectively attained. Although preferred embodiments of the invention have been disclosed and described in detail herein, it should be understood that this invention is in no sense limited thereby.

What is claimed is:

1. A radiological source, including:
a radiological insert with a toroidal shape and a central recess, the central recess terminating in a disk portion;
a shielding insert extending into the central recess; and
an encapsulation around the radiological insert.

2. The radiological source of claim 1 wherein the radiological insert includes strontium-90 contained in a material or compound selected from the group consisting of a strontium ceramic, a strontium glass, $SrF_2$, $Sr_2P_2O_7$, $SrTiO_3$, $SrO$, $Sr_2TiO_4$, $SrZrO_3$, $SrCO_3$, $Sr(NbO_3)^2$, $SrSiO_3$, $3SrO.Al_2O_3$, $SrSO_4$, $SrB_6$, $SrS$, $SrBr_2$, $SrC_2$, $SrCl_2$, $SrI_2$ and $SrWO_4$.

3. The radiological source of claim 1 wherein the disk portion is cylindrical.

4. The radiological source of claim 3 wherein the disk portion is centrally located within the radiological source.

5. The radiological source of claim 1 wherein the shielding insert is a portion of the encapsulation.

6. The radiological source of claim 5 wherein the shielding insert is a plateau structure on an interior lower floor of the encapsulation.

7. The radiological source of claim 6 wherein the plateau structure is rotationally symmetric.

8. The radiological source of claim 7 wherein the plateau structure has inclined sides.

* * * * *